(12) United States Patent
Bremauer (10) Patent No.: US 7,988,916 B2
(45) Date of Patent: Aug. 2, 2011

(54) APPARATUS FOR MIXING AND/OR TESTING SMALL VOLUMES OF FLUIDS

(76) Inventor: Ben Bremauer, Eltham (AU)

( * ) Notice: Subject to any disclaimer, the term of this patent is extended or adjusted under 35 U.S.C. 154(b) by 1635 days.

(21) Appl. No.: 10/513,918

(22) PCT Filed: May 7, 2003

(86) PCT No.: PCT/AU03/00539
§ 371 (c)(1),
(2), (4) Date: Nov. 8, 2004

(87) PCT Pub. No.: WO03/095952
PCT Pub. Date: Nov. 20, 2003

(65) Prior Publication Data
US 2005/0276724 A1    Dec. 15, 2005

(30) Foreign Application Priority Data
May 7, 2002  (AU) ........................................ PS 2298

(51) Int. Cl.
*G01N 31/16*        (2006.01)
(52) U.S. Cl. .............................. 422/75; 422/50; 422/105
(58) Field of Classification Search .................... 422/50, 422/67, 75, 105; 436/50, 55, 180
See application file for complete search history.

(56) References Cited

U.S. PATENT DOCUMENTS

| 3,953,136 A | 4/1976 | Hach |
| 4,141,250 A | 2/1979 | D'Autry |
| 4,205,953 A | 6/1980 | Miller |
| 4,663,126 A | 5/1987 | Gould et al. |
| 4,715,710 A | 12/1987 | Andersen |
| 4,861,451 A | 8/1989 | David |

(Continued)

FOREIGN PATENT DOCUMENTS

AU        B-33596/89        10/1990

(Continued)

OTHER PUBLICATIONS

Merriam Webster's Collegiate Dictionary, p. 5 (Tenth Edition, 1996).

(Continued)

*Primary Examiner* — Natalia Levkovich
(74) *Attorney, Agent, or Firm* — TraskBritt (57) ABSTRACT

An apparatus and method for measuring a range of small volumes of fluids to a high degree of precision, said apparatus including: a) a single reaction chamber (20); b) a piston (30) operable within said chamber to selectively and precisely vary the internal volume of said chamber; c) a first inlet (41) to said chamber in communication with one or more fluid sources of which a portion of a first fluid of said one or more fluids is adapted to be drawn into said chamber; d) at least one further inlet (43) including a second inlet to said chamber in communication with one or more fluid sources of which a portion of a second fluid of said one or more fluids is adapted to be drawn into said chamber; and e) a sealable outlet (45), wherein said piston is adapted to progressive draw said portion of a second fluid into said chamber until either accurare metering of a volume of said first or second portion of fluid is achived or a reaction involving said first and second portions in said chamber (such as a titration reaction) is completed.

15 Claims, 4 Drawing Sheets

U.S. PATENT DOCUMENTS

| | | | |
|---|---|---|---|
| 5,221,444 A | | 6/1993 | Silveri |
| 5,817,954 A | * | 10/1998 | Kahng et al. ............... 73/863.84 |
| 5,873,990 A | * | 2/1999 | Wojciechowski et al. .... 204/406 |
| 6,029,857 A | | 2/2000 | Keller |
| 6,071,408 A | * | 6/2000 | Allington et al. ............. 210/634 |
| 6,301,980 B1 | | 10/2001 | Munderloh |
| 7,658,824 B2 | | 2/2010 | Bremauer |

FOREIGN PATENT DOCUMENTS

| | | |
|---|---|---|
| AU | 74415/94 | 5/1995 |
| EP | 0 185 334 | 6/1986 |
| WO | WO 90/10734 | 9/1990 |
| WO | WO 96/11166 | 4/1996 |

OTHER PUBLICATIONS

Webster's Third New International Dictionary, p. 8 (1986).

The American Heritage College Dictionary, p. 6 (Third Edition, 2000).

* cited by examiner

APPARATUS FOR MIXING AND/OR TESTING SMALL VOLUMES OF FLUIDS

FIELD OF INVENTION

This invention relates to an apparatus for measuring the volume of small samples of fluids to a high degree of precision such as to within +/−0.05 to 0.03 mL. More particularly, this invention relates to an apparatus for precisely mixing and/or analysing small volumes of fluids for optic values. Still more particularly, this invention relates to an apparatus for reactants in exact stoichiametric ratios for the optimum production of a desired product; collecting fluid samples, reacting with a reagent in exact volume ratio and analysing for optic values; and/or for titration analysis of a fluid sample.

BACKGROUND ART

The requirement for automatic testing and chemical control of specific parameters in water and water bodies in the domestic, commercial and industrial sectors is increasingly demanded by both operators and governing bodies. The health risks associated with incorrectly managed pool or cooling tower water has created an awareness of the need for reliable automatic monitoring and treatment systems. Recent outbreaks of infection from the pathogens Giardia and Cryptosporidium contacted from commercial swimming pools and the numerous Legionella infections contracted from air conditioning water towers highlights the needs for stringent chemical testing. Government standards now often specify testing of commercial swimming pools or cooling towers be performed multiple times per day and the results must be entered into a log book for audit. Given the increasing awareness of bow important regular monitoring of water bodies such as swimming pools and cooling tows is, there is a need for an apparatus for mixing and/or testing small fluid samples which is capable of, at least to some extent, alleviating the often laborious task of regular testing and balance alteration.

Sanitisers generally used in the field of water treatment, such as the treatment of water cooling towers used in multistory buildings, domestic and public pools and spas, include chlorine, chlorine dioxide, hydrogen peroxide, ozone and bromine and combinations of these. The use of chlorine dioxide in the sanitisation of water is a relatively new phenomenon and is gaining popularity worldwide. It is especially effective against the pathogens, Giardia and Cryptosporidium and has been used extensively during outbreaks of these pathogens in swimming pools and drinking water during the year 2000 it Australia Chlorine dioxide must be produced in situ as it is unstable. For this reason, it is not sold in pre-packaged containers for consumer or commercial use. Chlorine dioxide is a dark yellow coloured gas. It may exist as gas dissolved in solution, but has a short shelf life. Principally there are two ways of producing chlorine dioxide, by the oxidation of chlorite or the reduction of chlorates. A simple method of production is to add sodium chloride to an acid in the correct proportions. However this process is particularly dangerous and it is not recommended that novices attempt to correctly mix the solutions. If the process is performed incorrectly, the chlorine dioxide gas may not remain dissolved in the solution and may evaporate out of solution to form a toxic gas cloud causing severe respiratory problems. Even relatively small airborne concentrations of chlorine dioxide may cause respiratory difficulties in those who su from asthma. Accordingly, there is a need for an apparatus capable of overcoming these safety issues to make available to novices the ability to use this excellent sanitiser chlorine dioxide, to treat the water body in question.

Automatic collection of samples of water for colormetric analysis has been limited to the use of flow through cells. These cells are normally used for colormetric analysis of the sample with any reagent introduced by means of a peristaltic pump. After introducing a reagent into the flow cell vial, a magnetic rod mixes the solution and the colorimetric analysis is performed. However, there is a concern with these flow through cells in applications such as swimming pools and spas where algae or mineral build up may line the inside of the cells whereby reducing their effectiveness by a affecting the optical transparency which they originally possessed. Consequently, inaccurate readings may result if regular cleaning of the cell is not performed. Accordingly, there is a need for an apparatus adapted for the colorimetric analysis of water samples using reagents which involves a less onerous cleaning regime.

Automatic control systems designed to test specific water parameters and react to correct the parameter that requires correction have been described, but are not necessarily widely known. These systems typically utilise probes and are usually positioned in the recirculating system associated with a water body to be treated the system interprets particular parameter values and, based on the results, a mechanical or electronic device may be activated to correct the value in question. The system may pump in liquid chlorine to increase the chlorine level or pump in hydrochloric acid to reduce the pH, for example.

In the case of swimming pools, spas and cooling towers, two water tests which may be automatically performed by this type of equipment are: (1) a measurement of the sanitiser level; and (2) a test of the pH level of the water. The correct control of these two parameters is most critical in preventing the growth of pathogens. Other tests may be required, but the prior art system using probes is not adapted to test parameters such as calcium hardness, total alkalinity and cyanuric acid or stabiliser levels. These tests are conventionally performed manually.

An oxidation redox potential (ORP) probe is typically used by these prior art devices to determine the redox potential or effectiveness of the sanitiser in question. The redox potential reading (expressed in millivolts) is dependent on the pH of the sample. A pH shift of only 0.5 mV upwards may result in excessive corrosive sanitiser levels developing. A downwards pH shift (more acidic) may result in inadequate sanitiser levels. Moreover, a correct chlorine determination and control becomes difficult with such ORP systems if the pH is not accurately monitored and stabilised. Another disadvantage is that the probes require regular cleaning and, furthermore, the instruments require regular calibration.

Whereas commercial operators may adhere to strict procedures which will help these ORP systems produce satisfactory results, novice user have been found to be less assiduous in following correct procedure. Moreover, many of these probes are very sensitive to the movement and velocity of water around them and minor alterations in localised water currents may effect the probe's ability to provide correct readings. Another disadvantage is that although this method may be useful in some instances, the redox potential output is not able to be interpreted in terms of parts per million in relation to sanitiser levels. As the person skilled in the art will appreciate, most world standards require that the sanitiser level be expressed in terms of parts per million. Accordingly, given the stands required in most jurisdictions, users of such ORP devices would still be required to perform standard manual sanitiser tests. In terms of commercial accessibility, ORP systems are expensive and generally out of the price range of the typical domestic pool owner.

As with ORP systems, an automatic method for pH testing using a pH probe has been described. The pH probe is placed in the water circuit and the pH is constantly monitored. An electric signal from the probe to a measuring device determines the pH and in situ in a water treatment plant, if the pH is outside a set range, normally a pump is activated to deliver a chemical to a system to correct the pH. These pH probes also require regular cleaning and become inaccurate if maintenance is ignored.

A disadvantage of both ORP and pH probes is that they are susceptible to producing incorrect values when hydrogen gas bubbles are in the test sample. The hydrogen gas interferes with the chemical reaction associated with the probe. Microscopic hydrogen bubbles are particularly evident in salt chlorination installations fitted to, for example, a pool. This very popular electrolytic method of chlorinating mild saline water systems produces hydrogen gas as a by product of the electrolytic reaction. It would be an advantage to have a colorimetric apparatus which is not affected by the presence of hydrogen gas in the test sample.

The above description of the prior art is not intended to be, nor should it be interpreted as, an indication of the common general knowledge pertaining to the invention, but rather to assist the person skilled in the art in understanding the developmental process which lead to the invention.

DISCLOSURE OF INVENTION

An apparatus for measuring a range of small volumes of fluids to a high degree of precision, said apparatus including:
  a) a single reaction chamber;
  b) a reciprocatable piston in said chamber;
  c) a first inlet to said chamber in communication with one or more fluid sources of which a portion of a first fluid of said one or more fluids is adapted to be drawn into said chamber;
  d) at least one further inlet including a second inlet to said chamber in communication with one or more fluid sources of which a portion of a second fluid of said one or more fluids is adapted to be drawn into said chamber; and
  e) a sealable outlet, wherein
  f) said piston is operable within said chamber to selectively and precisely vary the internal volume of said chamber, said internal volume including a minimal volume in which said chamber is substantially completely evacuated when said piston abuts a base of said chamber at a starting position;
  g) said first inlet has a first valve selectively operable to permit the flow of the first portion into said chamber by the movement of said piston within said chamber away from said base until a predetermined volume of said first fluid is drawn into said chamber;
  h) said second inlet has a second valve selectively operable to permit the flow of the second portion into said chamber by the movement of said piston within said chamber to progressively draw said second fluid into said chamber until a predetermined condition is met including the accurate metering of a volume of said second fluid or the completion of a reaction involving said first and second portions in said chamber;
  i) said piston is adapted to return to said starting position to substantially completely empty the contents of said chamber through said outlet; and
  j) said outlet is sealed by an outlet valve located in said base adjacent the internal surface of said chamber.

In another aspect, the invention provides an apparatus for testing a small volume of fluid said apparatus including:
  a) a testing chamber adapted for use with an optic value analyser;
  b) said optic value analyser adapted to transmit through said chamber;
  c) a piston operable within said chamber to selectively and precisely vary the volume of said chamber;
  d) a first inlet to said chamber in communication with a first source of a first fluid, said piston adapted to draw a first metered sample of said first fluid into said chamber;
  e) a second inlet to said chamber in communication with a reagent, said piston adapted to progressively draw in reagent until a predetermined condition is met; and
  e) a sealable outlet, wherein
  f) said first inlet is selectively adapted to permit the flow of said first sample into said chamber by the movement of said piston from a starting position to a first position;
  g) said second inlet is selectively adapted to permit the flow of said reagent into said chamber by the movement of said piston from said first position to a second position corresponding to said predetermined condition being met;
  h) said optic value analyser is adapted to test the contents of said chamber for at least one optic value; and
  i) said piston is adapted to return to said starting position to expel said contents through said outlet.

In yet another aspect of the invention, there is provided a method for testing a small volume of fluid, said method including the steps of:
  a) operating a piston to move said piston from a starting position to a first position to draw a predetermined and precise volume of a first fluid sample from a first fluid source through a first inlet of a testing chamber into said chamber;
  b) testing said first sample in said chamber for at least one optic value using an optic value analyser;
  c) returning said piston to said starting position whereby to expel said first sample through an outlet of said chamber.

In still another aspect of the invention, there is provided an apparatus for optically testing a small volume of a composition, said apparatus including:
  a) a chamber adapted for use with an optic value analyser;
  b) said optic value analyser adapted to transmit a signal through said chamber;
  c) a piston operable within said chamber to selectively and precisely vary the volume of said chamber;
  d) a first inlet in communication with said chamber which is, in turn, in communication with a first source of a firs fluid, said piston adapted to draw a first metered amount of said first fluid into said chamber through said first inlet by the movement of said piston to a second position;
  e) a second inlet in communication with said chamber which is, in turn, in communication with a second source of a second fluid, said piston adapted to draw a second metered amount of said second fluid into said chamber through a second inlet by the movement of said piston to a second position, which may constitute a predetermined condition being met; and
  f) a sealable outlet, wherein
  g) said first and second metered amounts combine to form said composition;
  h) said optic value analyser is adapted to test said composition for at least one optic value; and i) said piston is adapted to return to said starting position to expel said composition through said outlet.

In yet another aspect of the invention, there is provided a method for mixing a first and a second fluid in a closed system and delivering the resultant active composition to a water recirculation system, said method including the steps of:

a) opening a first inlet in communication with a chamber, whereby said chamber is placed in communication with a source of said first fluid;

b) operating a piston in said chamber to move said piston from a starting position, in which said piston abuts the internal surface of a base of said chamber, to a first position to draw a predetermined and precise volume of an amount of said first fluid from said first fluid source through said first inlet into said chamber;

c) closing said first inlet;

d) opening a second inlet in communication with said chamber, whereby said chamber is placed in communication with a source of said second fluid;

e) operating said piston to move said piston from said first position to a second position to draw a second fluid from said second fluid source through said second inlet into said chamber until a predetermined condition has been met;

f) closing said second inlet;

h) said first and second fluids combining to form said active composition;

i) returning said piston to said staring position whereby to substantially completely expel said active composition through a selectively operable outlet via an outlet valve located in said base and adjacent the internal surface of said chamber to said water recirculation system.

In yet another aspect of the invention there is provided a method for testing a small volume of a fluid composition, said method including the steps of:

a) opening a first inlet in communication with a chamber, whereby said chamber is placed in communication with a source of a first fluid;

b) operating a piston in said chamber to move said piston from a starting position, in which said piston abuts the internal surface of a base of said chamber, to a first position to draw a predetermined and precise volume of an amount of said first fluid from said first fluid source through said first inlet into said chamber;

c) closing said first inlet;

d) opening a second inlet in communication with said chamber, whereby said chamber is placed in communication with a source of a second fluid;

e) operating said piston to move said piston from said first position to a second position to draw a second fluid from said second fluid source through said second inlet into said chamber until a predetermined condition has been met, said first and second fluids mixing to form a composition;

f) closing said second inlet;

h) returning said piston to said starting position whereby to substantially completely expel said composition through a selectively operable outlet via an outlet valve located in said base and adjacent the internal surface of said chamber by returning said piston to said starting position abutting said internal surface of said base.

In a related aspect of the invention, there is provided a method for testing a small volume of a fluid composition, said method including the steps of:

a) opening a first inlet in communication with a chamber, whereby said chamber is placed in communication with a first fluid source;

b) operating a piston in said chamber to move said piston from a starting position to a first position to draw a predetermined and precise volume of a first fluid amount from said first fluid source through said first inlet into said chamber;

c) closing said first inlet;

d) opening a second inlet in communication with said chamber, whereby said chamber is placed in communication with a second fluid source;

e) operating said piston to move said piston from said first position to a second position to draw a predetermined and precise volume of a second fluid amount from said second fluid source through said second inlet into said chamber, which may constitute a predetermined condition having been met;

f) closing said second inlet;

g) said first and second fluid mount mixing or reacting to form a composition;

h) testing said composition with an optic value analyser to identify at least one optic value of said composition; and i) returning said piston to said starting position whereby to expel said composition through a selectively operable outlet of said chamber.

The predetermined condition may include any number of different conditions which, when satisfied cause the piton to cease moving away from the outlet. For example, the predetermined condition may correspond to the end point being reached in a titration procedure. The end point may be detected by the optic value analyser. Once the optic value analyser has detected the end point, the piston may be adapted to be stopped and the calibrated volume of reagent used to reach the end point recorded. The volume of reagent required may then be used to determine an appropriate treatment regime for the first fluid source. Alternatively, the predetermined condition may correspond to a pre-set volume of a fluid being drawn into the chamber. The fluid concerned may be the first, second or third fluid, etc., or may be a reagent. Once the pre-set volume of the fluid concerned is drawn into the chamber, the optic value analyser may be used to test the contents of the chamber for one or more optic values. Based on the one or more optic values identified, an appropriate treatment regime for the first fluid source may be determined.

The optic value analyser may include any suitable photometric device. Preferably, the optic value analyser is a colorimeter. Colorimeters suitable for the purpose are commercially available, but may also be purpose built using a suitable LED transmitter capable of transmitting, for example, a 555 nm signal capable of being received by a photoelectric sensor positioned on an opposed side of the chamber. The optic value analyser may be used to test for a number of parameters such as turbidity (such as may be done using prior art devices including flow through cells), but may also be used to test other parameters which require use of reagents and cannot be tested using flow through cells.

The first fluid is preferably water to be analysed and, if necessary, treated. However, the first fluid may be any other fluid, such as industrial gases or liquids, requiring precision mixing in a closed system or accurate analysis, involving procedures such as titration, to assess particular properties of the first fluid.

The first and/or second etc. inlets are preferably controlled by selectively operable first and/or second etc. valves. The apparatus may include a plurality of inlets in communication with containers of a plurality of reagents for use in testing the first fluid. Alternatively, the apparatus may include a single inlet, selectively in communication with a plurality of reagent containers. The plurality of inlets may be selectively shut off or opened by a corresponding plurality of valves, optionally controlled by a central processor.

The valves controlling the inlets may be operated manually. However, preferably the valves are operated by electric motors. Preferably the valves are operated by solenoids.

To prevent the ingress of debris which may interfere with reactions or testing in the chamber, the first inlet may include a filter to screen out solids and/or sludge suspended or otherwise borne in the first fluid. The filter may be planar mesh or may be convex or concave. The filter may be any suitable shape in cross-section, depending on the internal shape of the inlet. For example, the filter may be square, oval or circular in cross section. The filter may be cylindrical or otherwise basket shaped. The filter is preferably removable for cleaning.

The outlet may include any suitable valve device for permitting the removal of fluid from the chamber. The outlet preferably includes a one-way pressure valve. Preferably the outlet includes a spring-biased ball valve biased to a closed position and openable upon the movement of the piston from the first or second position, etc. to the starting position.

The second fluid may be a reactant or a reagent. Where the apparatus is used or the method involves the testing of fluid using the optic value analyser, the second fluid is preferably a reagent. Where the apparatus is used or the method involves the mixing of component reactants to form a fluid composition, the second fluid may be a reactant. The reagent is preferably adapted to react with the first fluid to produce a certain kind of optic value which may be read by the optic value analyser.

For example, chlorinated water from a pool, spa, cooling tower etc is drawn into the reaction chamber along with the reagent phenol red to react and develop a colour through which a colorimetric analysis is performed to give us the value for the pH of the water. A suitable light source and sensor is positioned on opposite sides of the clear reaction chamber. The wavelength of light best used is one which is most absorbed in the coloured sample. The phenol red indicator typically used for pH measurement in swimming pool and spa systems is applicable for testing the 6.8 to 8.4 pH range. The colour varies in this range from yellow to magenta and using a wavelength of 555 nm is typical for this colorimetric analysis. Typically the sample to reagent ratio is 293 parts sample to 1 part reagent with the phenol red reagent being 0.08%. The equipment is calibrated to interpret a processed voltage value corresponding to a numerical pH value. This value is then displayed. The device may perform two rinse cycles and perform a Free Chlorine test by mixing the water sample with the Free Chlorine reagents, DPD1 and DPD2 in the correct proportions. The intensity of the Magenta colour determines the Free Chlorine value. The same 555 nm light source, typically a suitable LED, is used.

Cyanuric acid levels would be tested in the chamber using a reagent that increases the turbidity of the sample in proportion to the cyanuric acid level in the sample. Melamine reagent may be used.

A photodiode positioned at right angles to the white light source, detects the scattered light and a calibrated voltage developed by the sensor and processed, is interpreted into a numerical cyanuric acid value in ppm.

The method for testing a small volume of a fluid composition may include a further step of treating the first fluid source in response to the at least one optic value reading obtained. Accordingly, the second fluid and further fluids may be provided which are chemicals adapted for treating certain parameters of the first fluid to bring those parameters back into a required range. Accordingly, the outlet may be selectively in communication with the first fluid. The apparatus may be adapted to draw a predetermined amount of the second fluid into the chamber and to deliver that specific amount to the first fluid source.

In another embodiment, the invention provides an apparatus for testing a small volume of a fluid composition, said apparatus including:
a) a testing chamber adapted for use with a calorimeter;
b) said colorimeter adapted to transmit a signal through said chamber;
c) a piston operable within said chamber to selectively and precisely vary the volume of said chamber;
d) a first inlet to said chamber in communication with a first source of a first fluid, said piston adapted to draw a first metered sample of said first fluid into said chamber; and
e) a sealable outlet, wherein
f) said first inlet is selectively adapted to permit the flow of said first sample into said chamber by the movement of said piston to a first position;
g) said calorimeter is adapted to test said first sample for optic values; and
h) said piston is adapted to return to a return position to expel said first sample through said outlet The apparatus may be controlled by a computer processor. The computer processor may be inbuilt or the apparatus may be adapted for connection to a computer. The computer processor preferably includes suitable software to control and coordinate the opening and closing of the one or more inlet valves and the operation of the piston.

In a particularly preferred embodiment, the invention relates to an apparatus which collects a fluid sample automatically, draws into the reaction chamber an appropriate colorimetric reagent, mixes the fluid sample and the reagent in the chamber and then performs a calorimetric analysis on the resulting sample.

In this preferred form of the invention, using the information from the calorimetric analysis, the apparatus may simply display the data, log the data or transfer the data via a computer interface. It may also initiate other mechanical or electronic apparatus to deliver a chemical to the water body or system to correct the parameter in question. After completion of the analysis, the calorimetric sample may be automatically discharged. The apparatus may then rinse the chamber once or many times by repeatedly drawing in and discharging the sample first fluid or a rinse fluid. Particularly, if a next and different reagent is to be introduced to the chamber through a different inlet, multiple rinses may be required to reduce the risk of contamination.

The apparatus may also perform automatic titration. For example, total alkalinity is tested in swimming pools. The apparatus may be used to auto-titrate to obtain a result for the total alkalinity in parts per million. The apparatus may sequence the titration by introducing the required water sample volume first, followed by the correct ratios of buffer solution and indicator. It may then slowly introduce the titrant until the colorimeter recognises the end point. A microprocessor may be used to control the apparatus and could be used to calculate the volume of reagent required to reach this end point and then the corresponding parts per million total alkalinity.

The apparatus also may lend itself to automatically performing a mixing function of sample and reagent(s) to obtain a colorimetric result. It may also perform the more complex mixing of sample, buffers, indicators and numerically determine the end point of a titration and thus the value of the concentration of the species being tested for. Because of this flexibility, in this preferred form, the apparatus may be configured such that not only is the chlorine and pH of a body of water automatically tested, but the whole range of reporting parameters. The other parameters which are normally required to be analysed are total alkalinity, calcium hardness, cyanuric acid, copper, iron, bromine, turbidity and numerous other parameters. Moreover, the apparatus may be configured for individual requirements.

The apparatus may perform such colorimetric tests in situ and may be in a format such that an external service company may use the apparatus to automatically test a customers fluid sample. The results may be processed by an integrated or interfaced computer. In this case, the apparatus would be unable to alter the water chemistry directly, but offers a computer print out of treatment recommendations.

In another particularly preferred aspect of the invention, the invention may provide an apparatus which is built such that it is a stand alone, fully integrated piece of equipment. Reaction chambers, reagents, computer processor and all the mechanical hardware may be self contained within this unit. The unit may include payment receiving means such as coin or card reader operated and supplied to customer access points, such as pool shops and hardware stores. The apparatus may be used as a tool to assist a customer in purchasing the correct chemicals in accordance with treatment recommendations. Accordingly, the apparatus would prompt the customer to pay. If the customer had previously used the apparatus, they may already be included on a data base and have been provided with a bar code on their sample body by the associated retailer. For first time users, a series of questions could be displayed to help the computer establish the volume of the water body in question, the type of lining of the container of the water body and any equipment details, such as whether salt chlorination or conventional chlorination is used. Other questions concerning the pool, spa, or water towers sanitation method, water condition and customer expectations might also be answered via a touch screen. As alluded to above, customers already on the data base would have the option of bypassing these introductory questions. A bar code reader may read a bar code applied to the sample container and parameters such as pool type and volume would automatically be uploaded for the computers consideration in carrying out calculations. The apparatus may prompt a user to position a sample bottle in a sample drawer chamber.

Once fitted, an apparatus or a plurality of such apparatus, could be used to draw a sample into the chamber, reacted with appropriate reagents and perform a colorimetric determination of the concentration of the tested species with a view to ultimately returning a processed numerical and written evaluation of the first fluid along with the chemical or mechanical corrections required to bring the water back into accepted parameters. Accordingly, the apparatus described obviates the need for skilled technicians to be in attendance.

The invention has obvious applications in the domestic swimming pool and spa market. Until now, the vast majority of domestic pool owners have been reliant upon themselves to manually test their pool and/or spa water. For the average person, this is yet another chore which interferes with their busy schedule and consequently regular testing is often not performed. When it is performed by the pool owner, often the subtleties of accurate testing are not adhered to resulting in a false or inaccurate result. This may lead the user to correct a water balance or sanitation parameter in an incorrect manner. Failure to test pool and/or spa water may not only result in water which is detrimental to the pool structure, pool equipment or swimmer comfort, but also to swimmer health. Incorrectly maintained low sanitiser levels, coupled with unchecked high pH may result in a body of water with little or no protection for a user against infection. These infections problems are exacerbated in heated spa water where the development of legionella is possible and, in fact, deaths have resulted from poor spa water maintenance.

The reagents which may be used with the apparatus include standard DPD chlorine test reagents as used in manual and calorimetric test kits. DPD1 refers to a free chlorine test using DPD2 (N,N-Diethyl-1,4-phenylene-diamine sulfate) and DPD1 which is a buffer solution which controls the pH of the sample in order for the DPD2 to react correctly and produce the desired magenta colour. Such reagents have a proven track record in testing for free and total chlorine and also facilitates the expression of results in parts per million. The value of the result is not affected by the pH of the sample and, unlike ORP systems, will not incorrectly alter the sanitiser level in the water if the pH is not within a tight parameter. The apparatus may use any number of test reagents to test for virtually any parameter required. Alternative sanitisers or tests may require the apparatus to introduce multiple reagents in the first fluid sample. Unlike ORP systems, there are no probes to meticulously clean, no probe current loop problems to contend with when used on salt water pools and is much cheaper and simpler to manufacture and maintain.

In another particularly preferred embodiment, the apparatus may be used to mix two or more reactants to produce a final composition. The apparatus may sequentially draw a predetermined volume of, for example, sodium chlorite solution into the reaction chamber, followed by a stoichiometrically correct acid volume. The two components would react to form chlorine dioxide, existing in a solution along with harmless by-products. Because the volumes are precisely measured, the efficiency of conversion to chlorine dioxide is optimised. As the entire reaction system is a closed system, not open to atmosphere, a release of chlorine dioxide gas to the atmosphere is not possible and the safely repercussions should be obvious. After the optimum reaction time within the reactor, the piston may be activated to force the chlorine dioxide through the outlet and into the water bodies recirculation system.

The piston may be operated in a number of ways. The piston may be controlled by an electric motor, capable of precise movements. Preferably the piston is driven by a worm drive which may be manually operated, but is preferably controlled by an electric motor. The piston may be adapted to clean the internal surface of the chamber when moving positions. The piston may include a peripheral flange, such as an annular lip. Preferably the piston includes at least two peripheral flanges either end of the piston head. The pair of peripheral flanges or the double lip may be made from a self-lubricating material. Preferably, the piston head, including the double lip, is made from Teflon. The chamber may be made from a scratch resistant glass. The piston may draw in fluid and subsequently discharge fluid whereby to constantly wipe the internal walls of the chamber thereby keeping them clean and free from organic and/or mineral build up.

The worm drive is preferably adapted to set the piston in one of a range of positions in the chamber. The worm drive may also be adapted to gradually move the piston through a range of positions during titration.

In another aspect the apparatus may further include
a) sample receiving means constituting the first fluid source for receiving the first fluid sample, either by means of a sample vessel placed on the receiving means or a recess into which a sample may be delivered such as by pouring, the sample receiving means being adapted to place the first fluid in communication with the chamber;

b) payment receiving means adapted to render the computer processing means operable
upon receiving a predetermined payment.

The apparatus may include a display and information input means. The apparatus may prompt the user for information concerning a number of predetermined values, such as first fluid source volume, inner surface material of vessel containing the first fluid source, existing treatment regime type, and provide feedback, preferably including feedback where nonsense values are entered by a user. The apparatus may conduct an analysis of the first fluid and provide one or more recommendations regarding treatment of the first fluid. The apparatus may include treatment means controlled by the computer processor which coordinates the treatment of the first fluid source in response to the results of the analysis performed by the optic value analyser.

BRIEF DESCRIPTION OF THE DRAWINGS

To more fully describe the invention, reference is made to the following non-limiting illustration namely.

DETAILED DESCRIPTION OF THE DRAWINGS

Figure 1:
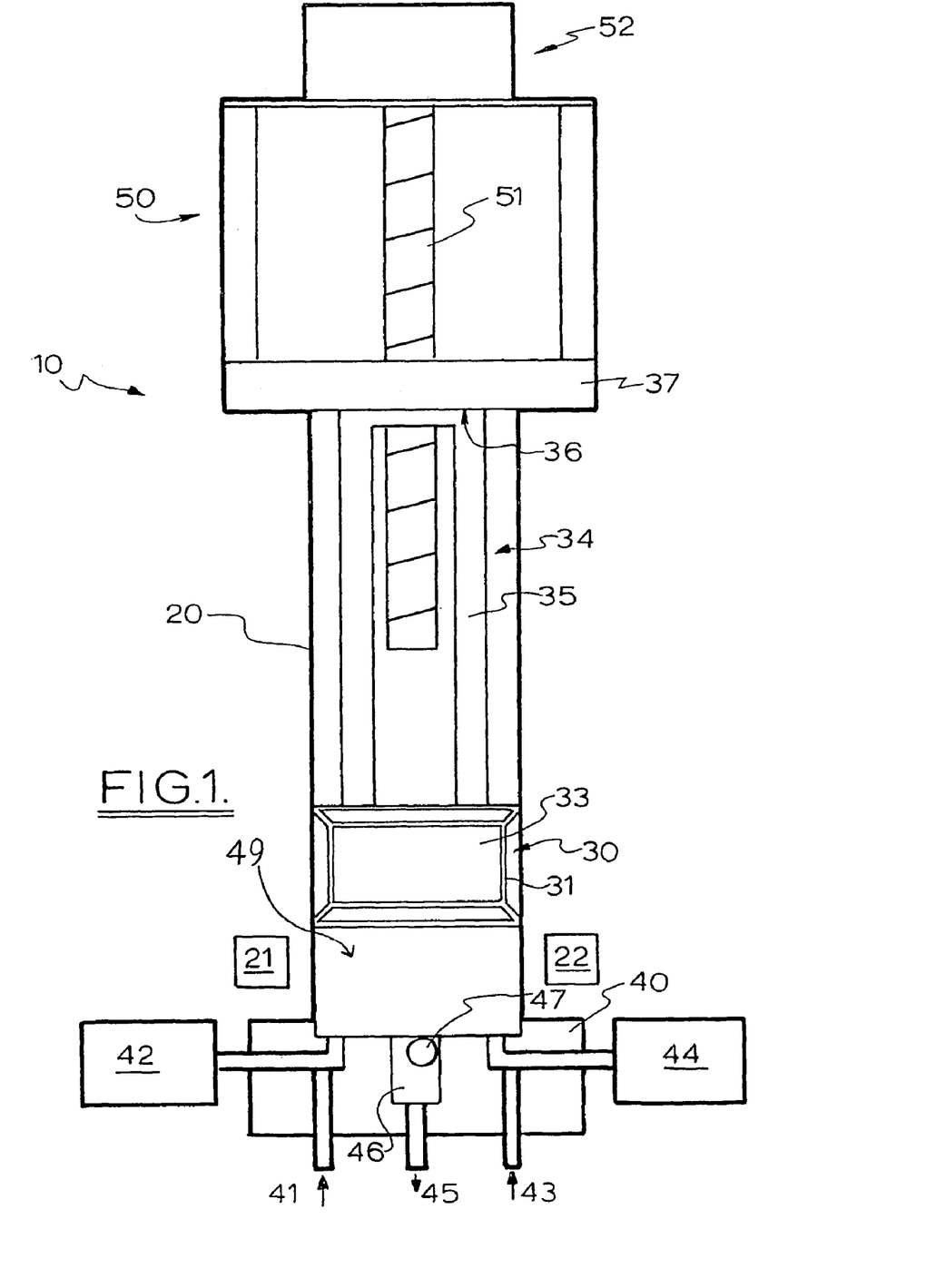
FIG. 1 is a schematic side view of an apparatus according to one embodiment of the invention.
Figures 4, 4A:
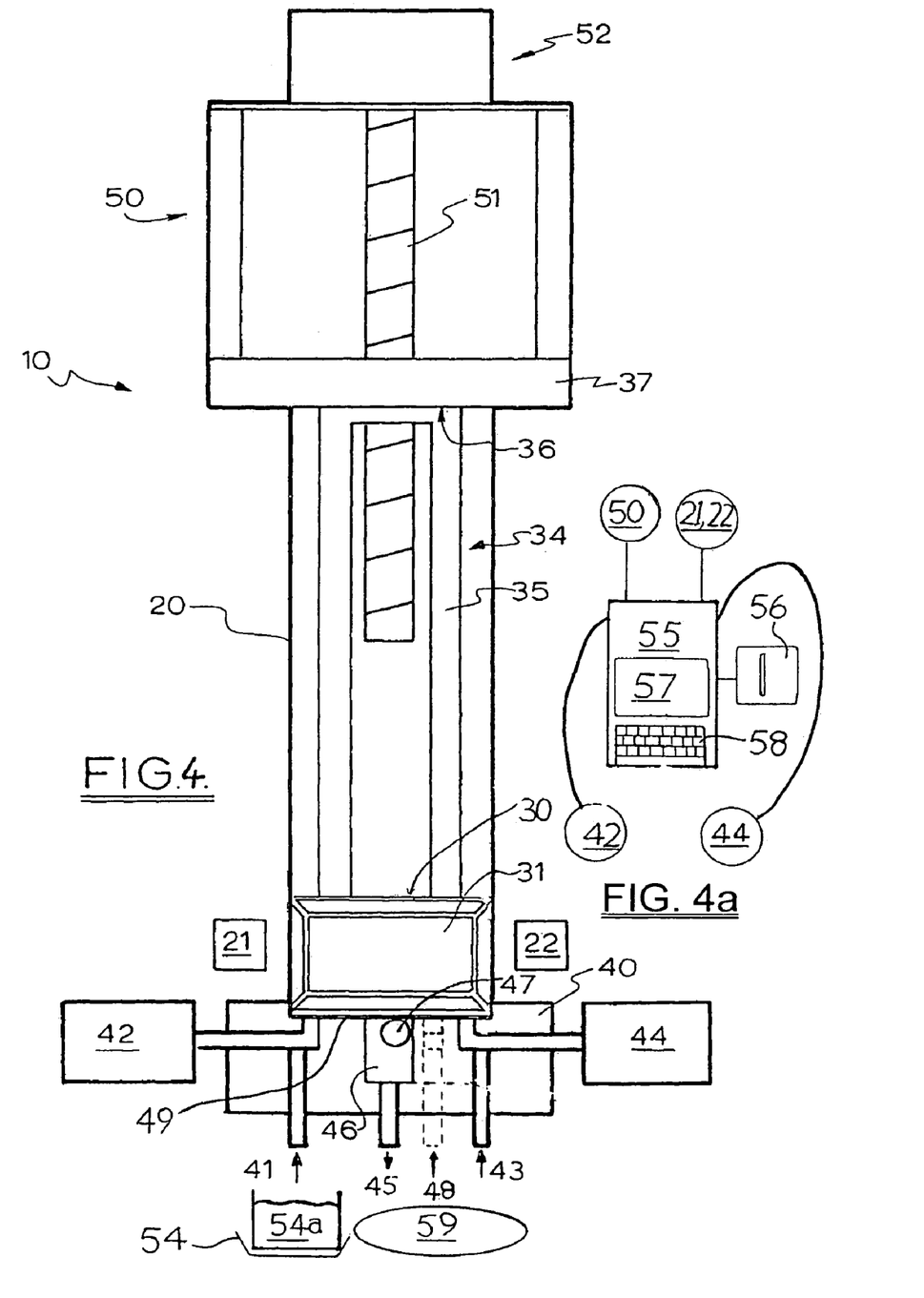
FIG. 4 is a schematic side view similar to that shown in FIG. 1.
FIG. 4a is a schematic illustration of a computer processor and the control and feedback connections to components of the apparatus shown in FIG. 4.

FIGS. 1 and 4 show shows an apparatus 10 including a chamber 20, a piston 30, a base 40, and a piston drive means 50.

The chamber 20 is a glass cylinder made from hardened, scratch resistant glass. Located near the base 40 of the chamber 20, is a calorimeter 21 including a LED (also reference numeral 21) and a photoelectric sensor 22 on the opposite side of the chamber to the LED 21.

The piston 30 includes a piston head 31, having a main body 32 in turn having an annular flange or lip 33 either end of the head 32. As the piston 30 translates up and down the chamber 20, the annular lips, made of Teflon, clean the chamber's internal glass surface, thereby providing an automatic cleaning mechanism for the internal surface of the chamber. The piston 30 includes a piston shaft 34, comprising a pair of elongate arms 35 extending between the piston head 32 and a bar 36 having a central threaded aperture 37.

A worm drive 51 cooperates with the threaded aperture 37 whereby the rotation of the worm drive 51 by a stepper motor 52 moves the piston 30 up or down the chamber 20. The piston 30 is operable within the chamber 20 to selectively and precisely vary the internal volume 49 of the chamber 20 defined by the piston 30, the base 40 and the internal wall of the chamber 20, the internal volume 49 including a minimal volume at a starting position (as shown in FIG. 4) in which the piston 30 abuts the base 40.

The base 40 is provided with a plurality of conduits including a first sample or reagent inlet port 41, selectively in communication with the internal space of the chamber 30 by the operation of a solenoid valve 42. The base further includes a second sample or reagent inlet port 43, selectively controlled by a second solenoid valve 44 to control the communication of the second inlet port to the chamber 20. The base 40 also includes the outlet 45 including a small recess 46 in which a spring biased ball valve 47 is located. The ball valve 47 is biased to a closed position and is opened by the application by positive pressure by the downward movement of the piston 30.

In FIGS. 4 and 4a, the apparatus 10 includes a third inlet 48 to the chamber 20 in communication with a third fluid source 59 of which a portion of the third fluid is adapted to be drawn into the chamber 20 by the operation of the piston 30, whereby the first fluid source is a source of a first reagent, the second fluid source is a source of a second reagent and the third fluid source 59 is a body of water. The first fluid source in communication with the first inlet 41 may be in the form of a user sample receiver 54 which puts the first fluid in communication with the chamber 20. The apparatus 10 may further include a payment receiving means in the form of a coin or card reader 56 (schematically shown) adapted to render a computer processor 55 (schematically shown) operable upon receiving a predetermined payment from the user. The sample receiver 54 receives the sample in a sample vessel 54a placed on the receiver 54 or in a recess into which the sample may be delivered such as by pouring. The computer processor 55 includes an information display 57 and input means 58. The display 58 is adapted to prompt the user for information concerning a number of predetermined values, including the third fluid source 59 volume, the inner surface material of the vessel 54a containing the third fluid source 59, existing treatment regime type, and to provide feedback including feedback where nonsense values are entered by the user.

It can be seen that the apparatus 10 may be used in a number of ways. The apparatus 10 may be used to draw a water sample in through inlet port 41 into the chamber up to a predetermined volume. The apparatus 10 controlled by the microprocessor 55, may then activate the solenoid valve 44 to draw a reagent in through the second inlet port 43. The volume of the reagent may be predetermined whereby, after a predetermined amount of time, the calorimeter 21 performs a reading and generates a result based on the specific volume of reagent drawn up by the piston 30. Alternatively, the apparatus 10 may perform a titration whereby the piston 30 constantly, gradually draws more reagent through the second inlet port 43 until the colorimeter 21 detects the end point. The results may be processed by the microprocessor 55 to provide treatment recommendations. To eject the tested sample from the chamber 20, the stepper motor 52 is activated to rotate the worm drive 51 to cause downward movement of the piston 30 until all of the sample is ejected through the outlet 45 to waste. The chamber 20 may be rinsed several times by drawing either water from the water body 59 or cleansing fluid through the first or second inlet port 41, 43 to flush out contaminants.

The apparatus 20 may then be used to draw in a treatment solution in an amount determined by the results of the colorimetric analysis through either the first or second inlet port 41, 43 and the treatment solution expelled into the water recirculation system via the outlet 45.

In another application of the apparatus 20, the apparatus may be used to mix reactants in a closed system and to deliver the resultant composition to the water recirculation system via the outlet 45 without exposing the reactants or the resultant composition to the atmosphere and, critically, to a user. Accordingly, chlorine dioxide may be produced and delivered to the a body of water 59 using the apparatus 20 by drawing in a precise amount of sodium chloride into the chamber 20 via inlet port 41, drawing a second reactant in the form of an acid in liquid form through inlet port 43 into the chamber 20 in a stoichiometrically predetermined ratio volume. The movement of the piston 30 through the first position to the second position, provides sufficient turbulence to mix the component reactants together and to produce a resultant chlorine dioxide solution. The downward travel of the piston 30 then forces the resultant chlorine dioxide solution through the outlet 45 and into the water recirculation system. This whole operation may be controlled by the microprocessor 55 whereby minimal human intervention is required.

Figure 2:
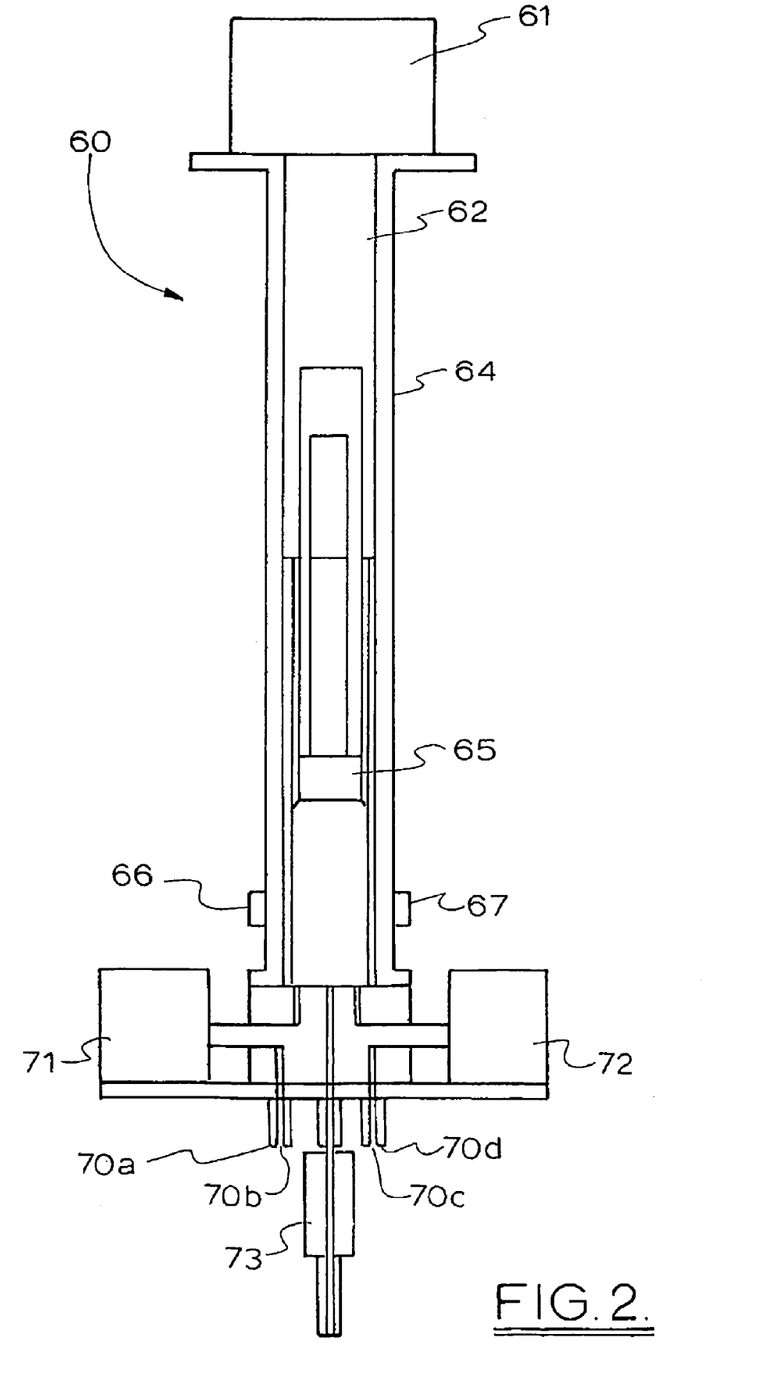
FIG. 2 is a schematic side view of an apparatus according to a second embodiment of the invention.

In FIG. 2 there is shown an auto sampling colorimeter 60 according to a second embodiment. The calorimeter 60 includes a DC step motor 61 adapted to drive a worm drive 62 which controls the reciprocal movement of a piston 63 and piston head 65 in a reaction chamber 64. The colorimetric measurements of the contents of the chamber 64 are carried out by the combined operation of a light emitting diode 66 on one side of the chamber and a diode or sensor 67 on the opposite side, both the LED 66 and sensor 67 being external to the glass or otherwise transparent wall of the chamber 64. The calorimeter 60 includes four inlet ports 70 a-d for introducing samples or reagents into the chamber 64. The valves controlling the communication of the inlet ports 60 a-d with the internal space of the chamber 64 are controlled by solenoids 71, 72, selectively operable according to inputs and programming of a central processor (not shown). Egress of the contents of the chamber is effected through a waste exit valve and port 73 at the base of the colorimeter 60.

Figure 3:
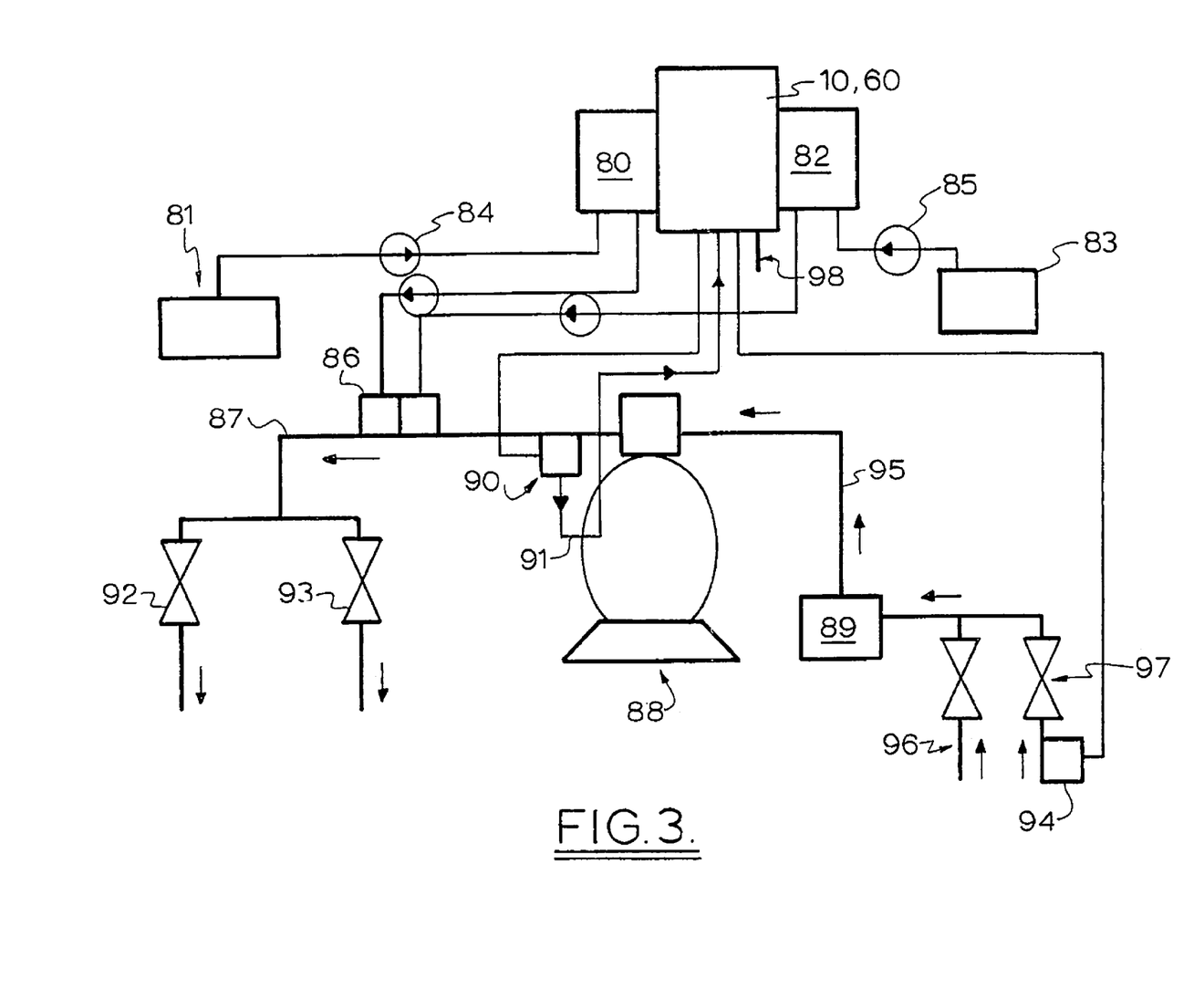
FIG. 3 is a system diagram showing the operation of an apparatus in accordance with one aspect of the invention.

FIG. 3 shows how an auto sampling colorimeter such as apparatus 10 or colorimeter 60 may be used in the maintenance of a body of water such as a pool or spa. Associated and adjacent the apparatus 10, 60 is a waste outlet 98 and a pair of pumps, a chlorine pump 80 for drawing chlorine from a chlorine drum 81 and an acid pump 82 for drawing acid from an acid drum 83. Check valves 84, 85 regulate flow from the respective drums 81, 83. Delivery to the water body is effected via an injection manifold 86 which delivers chlorine and acid solutions into the inlet stream corresponding to pipe 87. Pipe 87 transfers water from a filter 88 (having a pump 89 to convey water through the pipe 87). In-line in the pipe 87 is a main flow switch 90 and water sample feed line 91 which transfers water samples ex-filter 88 to the calorimeter 10, 60. Control valves 92, 93 control the delivery of treated water from the pipe 87 to the pool or spa. A spa flow switch 94 is determinative in cooperation with a central processor in indicating to the colorimeter 10, 60 when to switch over to a spa test sequence as opposed to a pool test sequence and whether a filter inlet pipe 95 takes water from the spa or the pool by the selective operation of control valves 96, 97.

When used in this specification and claims, the terms "comprises" and "comprising" and variations thereof mean that the specified features, steps or integers are included. The terms are not to be interpreted to exclude the presence of other features, steps or components.

The invention claimed is:

1. An apparatus for performing at least one of the operations of measuring, mixing, and analyzing a range of small volumes of fluids to a high degree of precision, said apparatus comprising:
    a single reaction chamber having a base;
    a reciprocatable piston in said chamber, an internal volume of said chamber extending between said piston and said base, said chamber having an internal surface;
    a first inlet to said chamber in communication with a first fluid source via a first valve from which a first fluid portion is adapted to be drawn into said chamber;
    a second inlet to said chamber in communication with a second fluid source via a second valve from which a second fluid portion is adapted to be drawn into said chamber;
    a sealable outlet, and a controller operatively connected to the piston, the first valve, and the second valve; wherein
    said piston is operable within said chamber to move between a starting position, a predetermined first position, and a predetermined second position to selectively and precisely vary the internal volume, said internal volume including a minimal volume in which said piston abuts said base at the starting position;
    wherein at the starting position the bottom surface of the piston is in direct contact with the base of the chamber; wherein movement of the piston to the first position permits flow of a predetermined volume of the first fluid portion through the first valve and into the chamber; wherein movement of the piston to the second position permits flow of a predetermined volume of the second fluid portion through the second valve and into the chamber; wherein;
    said piston is adapted to return to said starting position to eject all fluid contents in said chamber through said outlet; and
    wherein said outlet is sealed by an outlet valve located in said base adjacent the internal surface.

2. An apparatus according to claim 1, wherein said first and second inlets and said outlet are located in said base.

3. An apparatus according to claim 1, wherein said first and second valves are located in said base and said outlet valve is a one way pressure valve.

4. An apparatus according to claim 1, wherein said piston includes a pair of spaced annular lips.

5. An apparatus according to claim 1, wherein said apparatus includes a third inlet to said chamber in communication with a third fluid source of which a portion of said third fluid is adapted to be drawn into said chamber by the operation of said piston, whereby said first fluid source is a source of a first reagent, said second fluid source is a source of a second reagent and said third fluid source is a body of water.

6. An apparatus according to claim 1, further including an optic value analyzer adapted to optically analyze the fluid contents of said chamber.

7. An apparatus according to claim 6, wherein the controller comprises a computer processor connected to and controlling said optic value analyzer and the optic value analyzer indicates to the computer processor when said predetermined condition is met.

8. An apparatus according to claim 6, wherein the controller comprises a computer processor connected to and controlling a drive motor that drives the movement of said piston, a first electric motor to operate said first valve, a second electric motor to operate said second valve, and said optic value analyzer indicates to said computer processor when said predetermined condition is met.

9. An apparatus according to claim 1 or 5, wherein said first fluid portion is a first reagent and said second fluid portion is a second reagent, whereby said apparatus is connected to and controlled by the controller comprises a computer processor that controls:
    a drive motor that determines the movement of the piston; and
    a first and a second electric motor that respectively controls the first and second valves to mix and react together said first and second reagents in an accurate stoichiometric ratio to obtain an active composition.

10. An apparatus according to claim 9, wherein said first reagent is sodium chlorite, said second reagent is an acid in liquid form, said active composition includes chlorine dioxide and said apparatus provides a closed system for mixing said reactants without endangering a user.

11. An apparatus according to claim 9 when dependent on claim 5, wherein said outlet is in optionally in communication with a refuse disposal at the one time or a said body of water at another time via switch means and said apparatus is adapted to expel said active composition through said outlet via said outlet valve to said body of water.

12. An apparatus according to claim 8, wherein said first fluid source is in the form of a user sample receiving means which is adapted to place said first fluid in communication with said chamber; and said apparatus further includes payment receiving means connected to said computer processor, the payment receiving means configured to render the computer processor operable to the user upon receiving a predetermined payment from the user.

13. An apparatus according to claim 12, wherein said sample receiving means receives the sample in a sample vessel placed on said receiving means or in a recess into which the sample is delivered.

14. An apparatus according to claim 12, wherein said apparatus further includes an information display and input means.

15. An apparatus according to claim 14, wherein said display is adapted to prompt said user for information concerning a number of predetermined values, including the volume of a third fluid portion from a third fluid source, the inner surface material of a vessel containing said third fluid portion, existing treatment regime type, and to provide feedback including feedback where nonsense values are entered by said user.

\* \* \* \* \*